United States Patent
Moon

(10) Patent No.: US 11,534,057 B2
(45) Date of Patent: Dec. 27, 2022

(54) LIGHT SOURCE DEVICE, MEDICAL OBSERVATION SYSTEM, ILLUMINATION METHOD, AND COMPUTER READABLE RECORDING MEDIUM

(71) Applicant: Sony Olympus Medical Solutions Inc., Tokyo (JP)

(72) Inventor: Sojung Moon, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 265 days.

(21) Appl. No.: 16/798,432

(22) Filed: Feb. 24, 2020

(65) Prior Publication Data

US 2020/0288955 A1 Sep. 17, 2020

(30) Foreign Application Priority Data

Mar. 15, 2019 (JP) .............................. JP2019-049095

(51) Int. Cl.
| | |
|---|---|
| *A61B 1/06* | (2006.01) |
| *A61B 1/00* | (2006.01) |
| *H04N 9/31* | (2006.01) |
| *G03B 21/20* | (2006.01) |

(52) U.S. Cl.
CPC ........ *A61B 1/0638* (2013.01); *A61B 1/00009* (2013.01); *G03B 21/204* (2013.01); *G03B 21/2013* (2013.01); *G03B 21/2066* (2013.01); *H04N 9/3158* (2013.01)

(58) Field of Classification Search
CPC ... A61B 1/0638; A61B 1/0009; A61B 1/0655; A61B 1/00006; A61B 1/043; G03B 21/2013; G03B 21/204; G03B 21/2066; G03B 21/28; G03B 33/00; G03B 15/03; H04N 9/3158; H04N 9/3197
See application file for complete search history.

(56) References Cited

U.S. PATENT DOCUMENTS

| | | | |
|---|---|---|---|
| 2015/0009310 A1* | 1/2015 | Morimoto | A61B 1/00009 348/68 |
| 2015/0099932 A1* | 4/2015 | Morimoto | A61B 1/0684 315/153 |
| 2016/0022126 A1* | 1/2016 | Ramesh | A61B 1/045 600/109 |
| 2016/0058348 A1* | 3/2016 | Morimoto | A61B 1/000094 600/339 |

(Continued)

FOREIGN PATENT DOCUMENTS

JP 2013-215435 A 10/2013

*Primary Examiner* — John W Miller
*Assistant Examiner* — Sean N. Haiem
(74) *Attorney, Agent, or Firm* — Xsensus LLP

(57) ABSTRACT

A light source device includes: a first light source configured to emit first light including a white wavelength band or one or more wavelength bands of at least red, green, and blue; a second light source configured to emit second light including a specific wavelength band included in the first light; a first detector configured to detect an amount of the light of the specific wavelength band in the first light; a first optical member configured to multiplex light of a wavelength band different from the specific wavelength band in the first light, and the second light; and a processor configured to control the first light source based on a detection result of the first detector.

9 Claims, 8 Drawing Sheets

(56) References Cited

U.S. PATENT DOCUMENTS

2016/0143520 A1* 5/2016 Masaki ................ A61B 1/0638
                                                           600/109
2016/0231494 A1* 8/2016 Feingold .............. G02B 6/4298
2017/0188802 A1* 7/2017 Lawrence .............. A61B 1/128
2018/0042470 A1* 2/2018 Tanaka ...................... F21V 9/32
2018/0139370 A1* 5/2018 Ichiki ................... H04N 5/2354

* cited by examiner

LIGHT SOURCE DEVICE, MEDICAL OBSERVATION SYSTEM, ILLUMINATION METHOD, AND COMPUTER READABLE RECORDING MEDIUM

This application claims priority from Japanese Application No. 2019-049095, filed on Mar. 15, 2019, the contents of which are incorporated by reference herein in its entirety.

BACKGROUND

The present disclosure relates to a light source device, a medical observation system, an illumination method, and a computer readable recording medium.

In an endoscope system, a technique is known in which white light obtained by multiplexing light emitted from each of light emitting diode (LED) elements of red, green, and blue, and white light from a light emitter that emits light by receiving light from a laser diode (LD) element, on the same light path, is emitted towards a subject (for example, refer to JP 2013-215435 A). In this technique, an optical sensor is provided in the vicinity of the LD element, and a color balance of the white light is adjusted by controlling the amount of emitted light of each of the LED elements and the amount of emitted light of the LD element, based on a detection result from the optical sensor.

SUMMARY

In JP 2013-215435 A described above, the optical sensor indirectly detects the light emitted from the LD, and thus, the LD is not capable of accurately detecting the amount of emitted light, and therefore, there is a problem that the color balance is lost.

According to one aspect of the present disclosure, there is provided a light source device including: a first light source configured to emit first light including a white wavelength band or one or more wavelength bands of at least red, green, and blue; a second light source configured to emit second light including a specific wavelength band included in the first light; a first detector configured to detect an amount of the light of the specific wavelength band in the first light; a first optical member configured to multiplex light of a wavelength band different from the specific wavelength band in the first light, and the second light; and a processor configured to control the first light source based on a detection result of the first detector.

DETAILED DESCRIPTION

Figure 1:
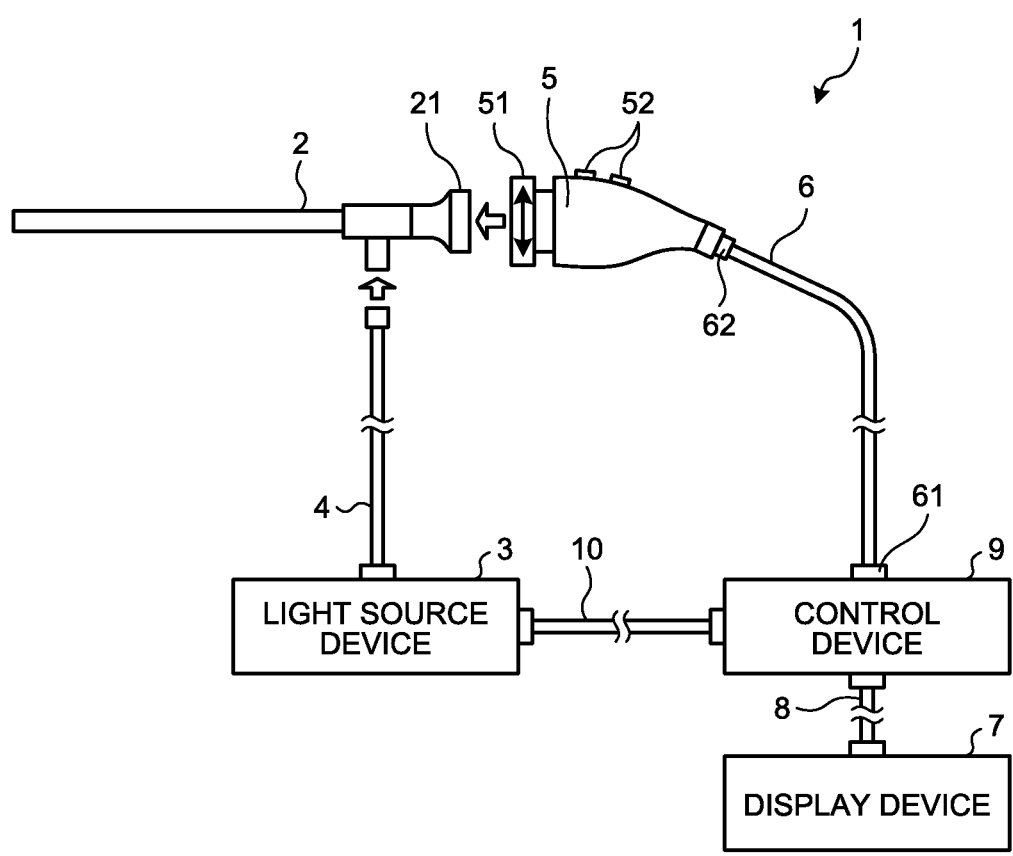
FIG. 1 is a diagram illustrating a schematic configuration of an endoscope system according to a first embodiment.

Hereinafter, modes for carrying out the present disclosure (hereinafter, referred to as "embodiments") will be described in detail, along with the drawings. Note that, the present disclosure is not limited to the following embodiments. In addition, the drawings referred to in the following description only schematically illustrate shapes, sizes, and positional relationships to the extent that the contents of the present disclosure can be understood. That is, the present disclosure is not limited to the shapes, the sizes, and the position relationships illustrated in each of the drawings. Further, in the description of the drawings, the same reference numerals will be applied to the same parts. In addition, an endoscope system will be described as an example of a medical observation system according to the present disclosure. In addition, in the description of the drawings, the same reference numerals will be applied to the same parts.

First Embodiment

Configuration of Endoscope System

FIG. 1 is a diagram illustrating a schematic configuration of an endoscope system according to a first embodiment. An endoscope system 1 illustrated in FIG. 1 is a device that is used in a medical field, is inserted into a subject such as a biological body of people or animals (into the biological body), and displays an image obtained by capturing the inside of the subject, and thus, observes the subject. Note that, in the first embodiment, a rigid endoscope system using a rigid endoscope (an insertion portion 2) illustrated in FIG. 1 is described as the endoscope system 1, but the present disclosure is not limited thereto, and for example, a flexible endoscope system may be used.

The endoscope system 1 illustrated in FIG. 1 includes the insertion portion 2 (an endoscope), a light source device 3, a light guide 4, a camera head 5 (an endoscopic imaging device), a first transmission cable 6, a display device 7, a second transmission cable 8, a control device 9, and a third transmission cable 10.

The insertion portion 2 is rigid or flexible in at least a part, has an elongated shape, and is inserted into the subject such as a patient. In the insertion portion 2, an optical system that is configured by using one or a plurality of lenses, and combines an observation image is provided.

One end of the light guide 4 is connected to the light source device 3. The light source device 3 emits (supplies) white light for illuminating the inside of the subject into one end of the light guide 4, and excitation light or infrared light toward a medical agent that is dosed to or dispersed in the subject, under the control of the control device 9. The light source device 3 is configured by using a light emitting diode (LED) light source or a semiconductor laser element such as a laser diode (LD). As illustrated in FIG. 1, the light source device 3 and the control device 9 may individually perform communication, or may be integrated.

One end of the light guide 4 is detachably connected to the light source device 3, and the other end is detachably connected to the insertion portion 2. The light guide 4 guides light emitted from the light source device 3 to the other end from one end, and supplies the light to the insertion portion 2.

An eye piece 21 of the insertion portion 2 is detachably connected to the camera head 5. The camera head 5 generates an imaging signal by capturing the observation image that is formed by the insertion portion 2, and outputs the imaging signal (an electric signal), under the control of the control device 9. In addition, the camera head 5 includes a manipulation ring portion 51 that is provided to be rotatable in a circumference direction, and a plurality of input units 52 that receive the input of an instruction signal for instructing various manipulations of the endoscope system 1.

One end of the first transmission cable 6 is detachably connected to the control device 9 through a first connector portion 61, and the other end is connected to the camera head 5 through a second connector portion 62. The first transmission cable 6 transmits the imaging signal that is output from the camera head 5 to the control device 9, and transmits a control signal, a synchronization signal, a clock signal, power, and the like that are output from the control device 9 to the camera head 5.

The display device 7 may be connected to the control device 9 through the second transmission cable 8, and displays a medical agent observation image corresponding to medical agent observation image information, a subject observation image corresponding to subject observation image information, various information items relevant to the endoscope system 1 that are processed by the control device 9, under the control of the control device 9.

One end of the second transmission cable 8 is detachably connected to the display device 7, and the other end is detachably connected to the control device 9. The second transmission cable 8 transmits a display image based on an image signal that is processed in the control device 9 to the display device 7.

The control device 9 is configured by using a processor including a memory, and hardware such as a central processing unit (CPU), a graphics processing unit (GPU), an application specific integrated circuit (ASIC), and a field programmable gate array (FPGA), and comprehensively controls the operation of the light source device 3, the camera head 5, and the display device 7 through each of the first transmission cable 6, the second transmission cable 8, and the third transmission cable 10, in accordance with a program recorded in the memory.

One end of the third transmission cable 10 is detachably connected to the light source device 3, and the other end side is detachably connected to the control device 9. The third transmission cable 10 transmits the control signal from the control device 9 to the light source device 3.

Configuration of Light Source Device

Figure 2:
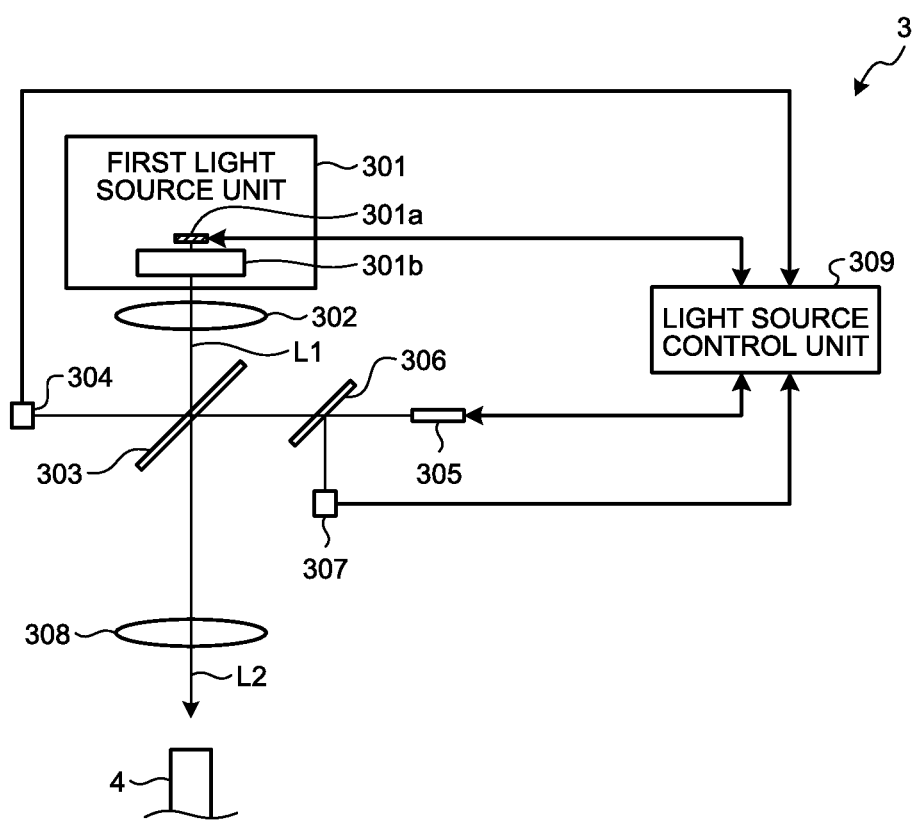
FIG. 2 is a schematic view illustrating a schematic configuration of a light source device according to the first embodiment.

Next, the detailed configuration of the light source device 3 will be described. FIG. 2 is a schematic view illustrating a schematic configuration of the light source device 3. The light source device 3 includes a first light source unit 301, a first condenser lens 302, a first optical member 303, a first detecting unit 304, a second light source unit 305, a second optical member 306, a second detecting unit 307, a second condenser lens 308, and a light source control unit 309.

The first light source unit 301 emits first light including a white wavelength band (400 nm to 750 nm) under the control of the light source control unit 309. Specifically, the first light source unit 301 emits the first light towards a light path L2 on which the first light and the other light are multiplexed. The first light source unit 301 includes a blue LED element 301a that emits light of a blue wavelength band (a wavelength band of 435 nm to 480 nm), and a yellow fluorescent body 301b that emits white light by receiving blue light that is emitted from the blue LED element 301a. Note that, it is sufficient that the first light source unit 301 may emit the white light as the first light, and the first light source unit 301, for example, may be a white light LED element, a light emitting element including a violet LED that emits light of a violet wavelength band and a fluorescent body that emits white light by receiving violet light, a xenon lamp, or the like.

The first condenser lens 302 condenses and emits the first light that is emitted from the first light source unit 301. The first condenser lens 302 is configured by using one or a plurality of lenses.

The first optical member 303 is configured by using a reflection filter such as dichroic mirror, and is disposed on a light path L1 before the light path L2 on which the first light and the other light are multiplexed. The first optical member 303 multiplexes light of a wavelength band different from a specific wavelength band in the first light emitted from the first light source unit 301 through the first condenser lens 302, and second light including the specific wavelength band included in the first light emitted from a second light source unit 305 described below to emit towards the second condenser lens 308. Specifically, the first optical member 303 emits (reflects) the light of the specific wavelength band in the first light emitted from the first light source unit 301 through the first condenser lens 302 towards the first detecting unit 304, and multiplexes the light of the wavelength band different from the specific wavelength band in the first light, and the second light including the specific wavelength band included in the first light emitted from the second light source unit 305 described below towards the second condenser lens 308. More specifically, the first optical member 303 reflects light a red wavelength band included in the first light (a wavelength band of 600 nm to 700 nm) to the first detecting unit 304, and transmits light of a wavelength band different from the red wavelength band.

The first detecting unit 304 is configured by using an optical sensor such as a photodiode. The first detecting unit 304 detects the amount of light of the specific wavelength band in the first light emitted from the first optical member 303, and outputs the detection result to the light source control unit 309. Specifically, the first detecting unit 304 detects the amount of light of the red wavelength band included in the first light emitted from the first optical member 303, and outputs the detection result to the light source control unit 309.

The second light source unit 305 emits the second light of the specific wavelength band included in the first light emitted from the first light source unit 301 under the control of the light source control unit 309. Specifically, the second light source unit 305 emits the second light towards the first optical member 303 under the control of the light source control unit 309. Here, the second light is light for the first light source unit 301 to compensate the light of the specific wavelength band reflected by the first optical member 303. Specifically, the second light source unit 305 emits the light of the red wavelength band as the second light. The second light source unit 305 is configured by using a red LD element or fiber that may emit red light.

The second optical member 306 is configured by using a reflection filter such as dichroic mirror. The second optical member 306 is disposed between the first optical member 303 and the second light source unit 305. The second optical member 306 reflects a part of the second light emitted from the second light source unit 305 towards the second detecting unit 307, and transmits the remaining light towards the first optical member 303.

The second detecting unit 307 is configured by using an optical sensor such as a photodiode, detects the amount of a part of the second light reflected by the second optical member 306, and outputs the detection result to the light source control unit 309.

The second condenser lens 308 condenses and emits light that is multiplexed by the first optical member 303 on the light path L2 into the light guide 4. Specifically, the second condenser lens 308 condenses the light in which the light of the wavelength band different from the specific wavelength band in the first light emitted from the first light source unit 301 through the first condenser lens 302, and the second light that is transmitted through the second optical member 306 are multiplexed by the first optical member 303 and emitted into the insertion portion 2 (the endoscope) through the light guide 4. The second condenser lens 308 is configured by using one or a plurality of lenses.

The light source control unit 309 is configured by using a processor including a memory and hardware such as a central processing unit (CPU), a field programmable gate array (FPGA), and an application specific integrated circuit (ASIC). The light source control unit 309 controls the amount of emitted light from each of the first light source unit 301 and the second light source unit 305, based on the detection result of each of the first detecting unit 304 and the second detecting unit 307. Specifically, the light source control unit 309 controls the amount of emitted light from the first light source unit 301, based on the detection result of the first detecting unit 304, and thus, controls the brightness of the white light emitted from the first light source unit 301. In addition, the light source control unit 309 controls a color taste of the second light emitted from the second light source unit 305 the amount of emitted light emitted from each of the first light source unit 301 and the second light source unit 305 is at a constant ratio, based on the detection result each of the first detecting unit 304 and the second detecting unit 307. Note that, in the first embodiment, the light source control unit 309 functions as a processor.

Processing of Light Source Device

Figure 3:
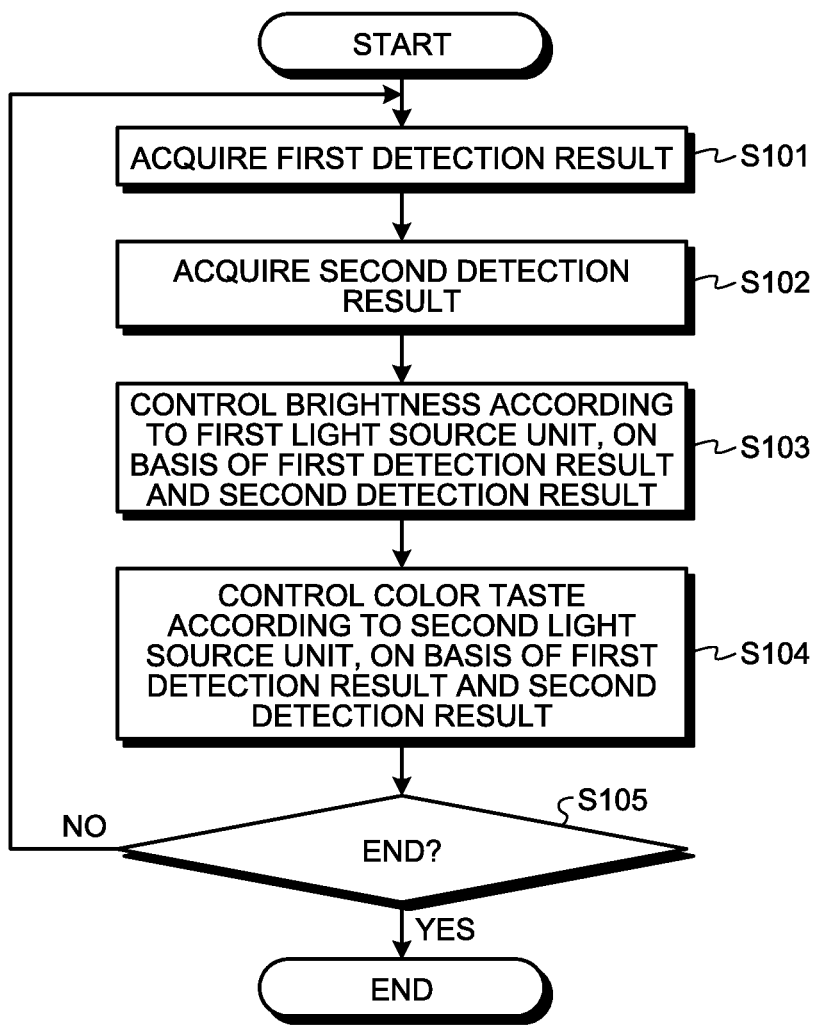
FIG. 3 is a flowchart illustrating an outline of processing that is executed by the light source device according to the first embodiment.

Next, processing that is executed by the light source device 3 will be described. FIG. 3 is a flowchart illustrating the outline of the processing that is executed by the light source device 3.

As illustrated in FIG. 3, first, the light source control unit 309 acquires the detection result of the first detecting unit 304 (Step S101), and acquires the detection result of the second detecting unit 307 (Step S102).

Subsequently, the light source control unit 309 controls a brightness according to the first light source unit 301, based on the detection result acquired from the first detecting unit 304 and the detection result acquired from the second detecting unit 307 (Step S103). Specifically, the light source control unit 309 adjusts a drive current to be supplied to the first light source unit 301, and a light emitting time, based on the detection result acquired from the first detecting unit 304 and the detection result acquired from the second detecting unit 307, and thus, controls the amount of white light emitted from the first light source unit 301 such that the white light has a predetermined brightness. Accordingly, it is possible to maintain a color balance and a brightness of the white light.

After that, the light source control unit 309 controls a color taste according to the second light source unit 305, based on the detection result acquired from the first detecting unit 304 and the detection result acquired from the second detecting unit 307 (Step S104). Specifically, the light source control unit 309 adjusts a drive current to be supplied to the second light source unit 305, and a drive time, based on the detection result acquired from the first detecting unit 304 and the detection result acquired from the second detecting unit 307, and thus, controls the amount of light emitted from the second light source unit 305 such that the white light has a predetermined color taste, and therefore, the color taste or the color balance of the white light is adjusted.

Subsequently, when an instruction signal for instructing the end of the observation of the subject is input from the control device 9 (Step S105: Yes), the light source device 3 ends the processing. In contrast, when the instruction signal for instructing the end of the observation of the subject is not input from the control device 9 (Step S105: No), the light source device 3 returns to Step S101 described above.

According to the first embodiment described above, the first optical member 303 multiplexes the light of the wavelength band different from the specific wavelength band in the first light emitted from the first light source unit 301, and the second light of the specific wavelength band included in the first light emitted from the second light source unit 305, and the light source control unit 309 controls the first light source unit 301, based on the detection result of the first detecting unit 304, and thus, it is possible to maintain the color balance or the brightness of the white light.

In addition, according to the first embodiment, the light source control unit 309 controls the first light source unit 301 and the second light source unit 305, based on the detection result of the first detecting unit 304 and the detection result of the second detecting unit 307, and thus, it is possible to maintain the color balance or the color taste of the white light.

Second Embodiment

Next, a second embodiment will be described. The second embodiment is different from the first embodiment described above in the configuration of the light source device 3. Hereinafter, the configuration of a light source device according to the second embodiment will be described. Note that, the same reference numerals will be applied to the same configurations as those of the endoscope system 1 according to the first embodiment described above, and the detailed description thereof will be omitted.

Detailed Configuration of Light Source Device

Figure 4:
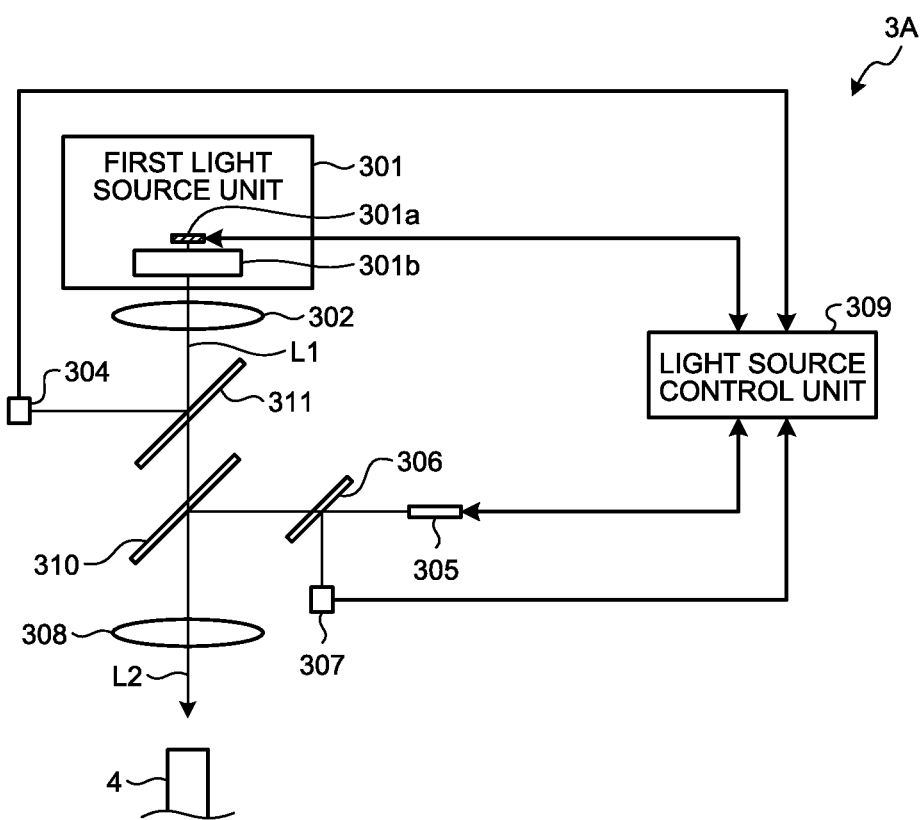
FIG. 4 is a schematic view illustrating a schematic configuration of a light source device according to a second embodiment.

FIG. 4 is a schematic view illustrating a schematic configuration of the light source device according to the second embodiment. A light source device 3A illustrated in FIG. 4 includes a first optical member 310, instead of the first optical member 303 of the light source device 3 according to the first embodiment described above. Further, the light source device 3A further includes a third optical member 311.

The third optical member 311 is configured by using a reflection filter such as dichroic mirror, and is disposed on the light path L1 of the first light between the first light source unit 301 and the first optical member 310. The third optical member 311 emits the light of the specific wavelength band in the first light emitted from the first light source unit 301 through the first condenser lens 302 into the first detecting unit 304, and the light of the wavelength band different from the specific wavelength band in the first light into the first optical member 310. Specifically, the third optical member 311 emits (reflects) the light of the red wavelength band included in the first light into the first detecting unit 304, and emits (transmits) the light of the wavelength band different from the red wavelength band in the first light into the first optical member 310.

The first optical member 310 multiplexes the light of the wavelength band different from the specific wavelength band in the first light emitted from the third optical member 311, and the second light including the specific wavelength band included in the first light emitted from the second optical member 306 to emit towards the second condenser lens 308.

According to the second embodiment described above, the light source control unit 309 controls the first light source unit 301 and the second light source unit 305, and thus, as with the first embodiment described above, it is possible to maintain the color balance, the brightness, and the color taste of the white light.

Third Embodiment

Next, a third embodiment will be described. In the third embodiment, the configuration of the light source device is different. Hereinafter, the configuration of a light source device according to the third embodiment will be described. Note that, the same reference numerals will be applied to the same configurations as those of the endoscope system 1 according to the first embodiment described above, and the detailed description thereof will be omitted.

Configuration of Light Source Device

Figure 5:
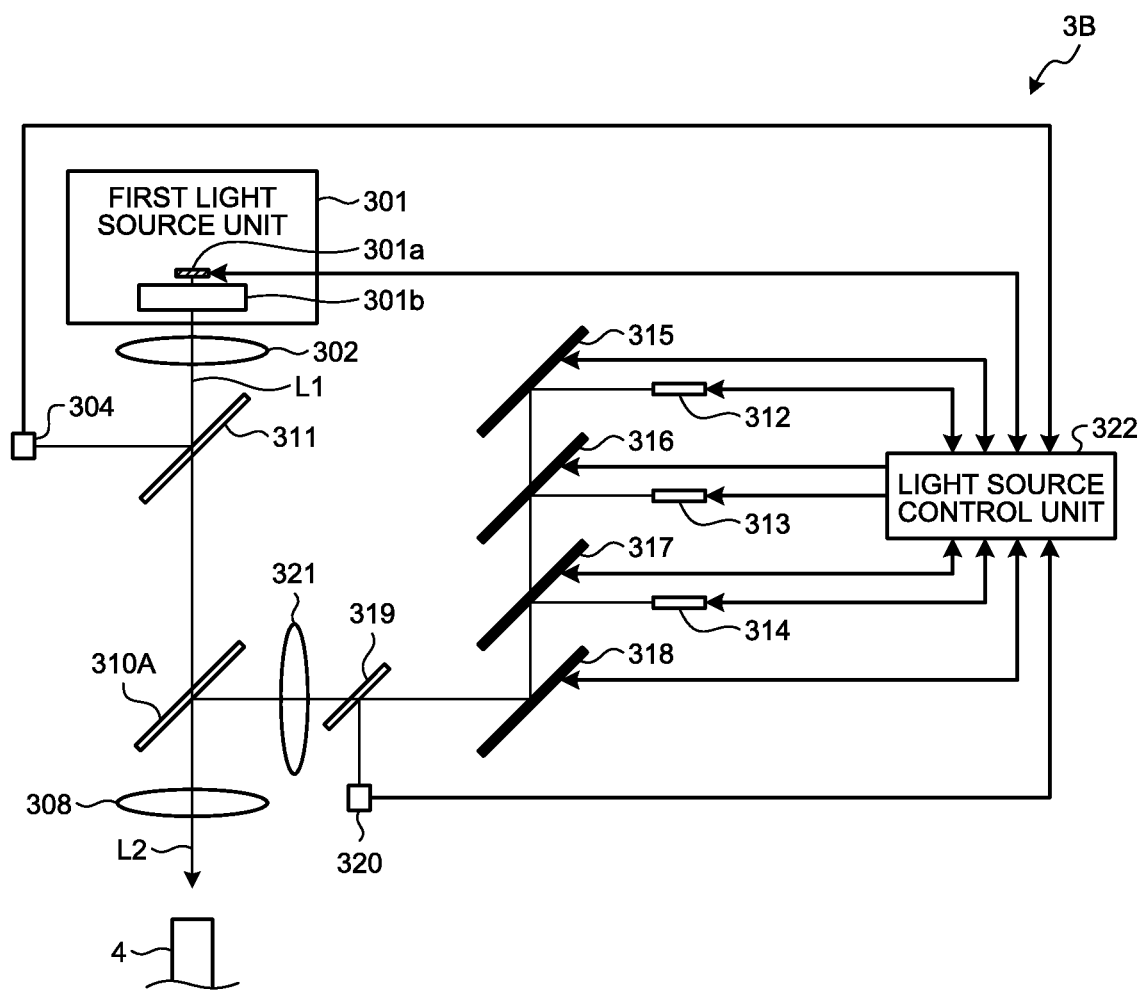
FIG. 5 is a schematic view illustrating a schematic configuration of a light source device according to a third embodiment.

FIG. 5 is a schematic view illustrating a schematic configuration of the light source device according to the third embodiment. A light source device 3B illustrated in FIG. 5 includes the first light source unit 301, the first condenser lens 302, the first detecting unit 304, the second condenser lens 308, and the third optical member 311. Further, the light source device 3B includes a first optical member 310A, instead of the first optical member 310 according to the second embodiment described above. In addition, the light source device 3B includes a second light source unit 312, a third light source unit 313, a fourth light source unit 314, a first variable shape mirror 315, a second variable shape mirror 316, a third variable shape mirror 317, a fourth variable shape mirror 318, a second optical member 319, a second detecting unit 320, a third condenser lens 321, and a light source control unit 322.

The second light source unit 312 emits light of a blue wavelength band (a wavelength band of 400 nm to 500 nm) under the control of the light source control unit 322. The second light source unit 312 is configured by using a blue LD element or fiber that may emit blue light.

The third light source unit 313 emits light of a green wavelength band (a wavelength band of 500 nm to 600 nm) under the control of the light source control unit 322. The third light source unit 313 is configured by using a green LD element or fiber that may emit green light.

The fourth light source unit 314 emits the light of the red wavelength band (a wavelength band of 600 nm to 700 nm) under the control of the light source control unit 322. The fourth light source unit 314 is configured by using the red LD element or fiber that may emit the red light.

The first variable shape mirror 315 reflects the blue light emitted from the second light source unit 312 towards the fourth variable shape mirror 318. The first variable shape mirror 315 is configured by using piezo element type variable shape mirror. The first variable shape mirror 315 may be changed into a predetermined shape by a driving unit such as a motor (not illustrated), under the control of the light source control unit 322.

The second variable shape mirror 316 reflects the green light emitted from the third light source unit 313 towards the fourth variable shape mirror 318. The second variable shape mirror 316 is configured by using piezo element type variable shape mirror. The second variable shape mirror 316 may be changed into a predetermined shape by a driving unit such as a motor (not illustrated), under the control of the light source control unit 322.

The third variable shape mirror 317 reflects the red light emitted from the fourth light source unit 314 towards the fourth variable shape mirror 318. The third variable shape mirror 317 is configured by using piezo element type variable shape mirror. The third variable shape mirror 317 may be changed into a predetermined shape by a driving unit such as a motor (not illustrated), under the control of the light source control unit 322.

The fourth variable shape mirror 318 reflects the second light including the specific wavelength band included in the first light that is the second light in which the light rays reflected from the first variable shape mirror 315, the second variable shape mirror 316, and the third variable shape mirror 317 are multiplexed towards the second optical member 319. The fourth variable shape mirror 318 is configured by using piezo element type variable shape mirror. The fourth variable shape mirror 318 may be changed into a predetermined shape by a driving unit such as a motor (not illustrated), under the control of the light source control unit 322.

The second optical member 319 is configured by using a reflection filter such as dichroic mirror, and is disposed between the first optical member 310A and the fourth variable shape mirror 318, that is, between the first optical member 310A and the second light source unit 312. The second optical member 319 reflects a part of the second light that is multiplexed by the fourth variable shape mirror 318 to the second detecting unit 320, and transmits the remaining light to the third condenser lens 321. Specifically, the second optical member 319 reflects a part of the light of the red wavelength band that is light of the same wavelength band as that of the light of the specific wavelength band in the first light reflected by the third optical member 311 towards the second detecting unit 320.

The second detecting unit 320 is configured by using an optical sensor such as a photodiode, detects the amount of a part of the second light reflected by the second optical member 319, and outputs the detection result to the light source control unit 322.

The third condenser lens 321 condenses and emits light that is transmitted through the second optical member 319 into the first optical member 310A. The third condenser lens 321 is configured by using one or a plurality of lenses.

The first optical member 310A is configured by using a reflection filter such as dichroic mirror. The first optical member 310A multiplexes the light of the wavelength band different from the specific wavelength band in the first light emitted from the third optical member 311, and the second light including the specific wavelength band included in the first light emitted from the second optical member 306 through the third condenser lens 321 to emit towards the second condenser lens 308.

The light source control unit 322 is configured by using a processor including a memory and hardware such as a CPU, an FPGA, and an ASIC. The light source control unit 309 controls the amount of emitted light from each of the first light source unit 301, the second light source unit 312, the third light source unit 313, and the fourth light source unit 314, based on the detection result of each of the first detecting unit 304 and the second detecting unit 320. Specifically, the light source control unit 322 performs control such that the amount of emitted light from each of the first light source unit 301, the second light source unit 312, the third light source unit 313, and the fourth light source unit 314 is at a constant ratio, based on the detection result of each of the first detecting unit 304 and the second detecting unit 320. Note that, the light source control unit 322 performs the same processing as that of the light source control unit 309 according to the first embodiment described above.

According to the third embodiment described above, the light source control unit 322 controls the first light source unit 301, the second light source unit 312, the third light source unit 313, and the fourth light source unit 314, based on the detection result of the first detecting unit 304 and the detection result of the second detecting unit 320, and thus, as with the first embodiment described above, it is possible to maintain the color balance, the brightness, and the color taste of the white light.

Note that, in the third embodiment, the third optical member 311 and the second optical member 319 reflect a part of the light of the red wavelength band, but the present disclosure is not limited thereto, and for example, optical properties of the third optical member 311 and the second optical member 319 may be changed to optical properties in which a part of the light of the green wavelength band or the light of the blue wavelength band is reflected.

Fourth Embodiment

Next, a fourth embodiment will be described. In the fourth embodiment, the configuration of the light source device is different. Hereinafter, the configuration of a light source device according to the fourth embodiment will be described. Note that, the same reference numerals will be applied to the same configurations as those of the endoscope system 1 according to the first embodiment described above, and the detailed description thereof will be omitted.

Configuration of Light Source Device

Figure 6:
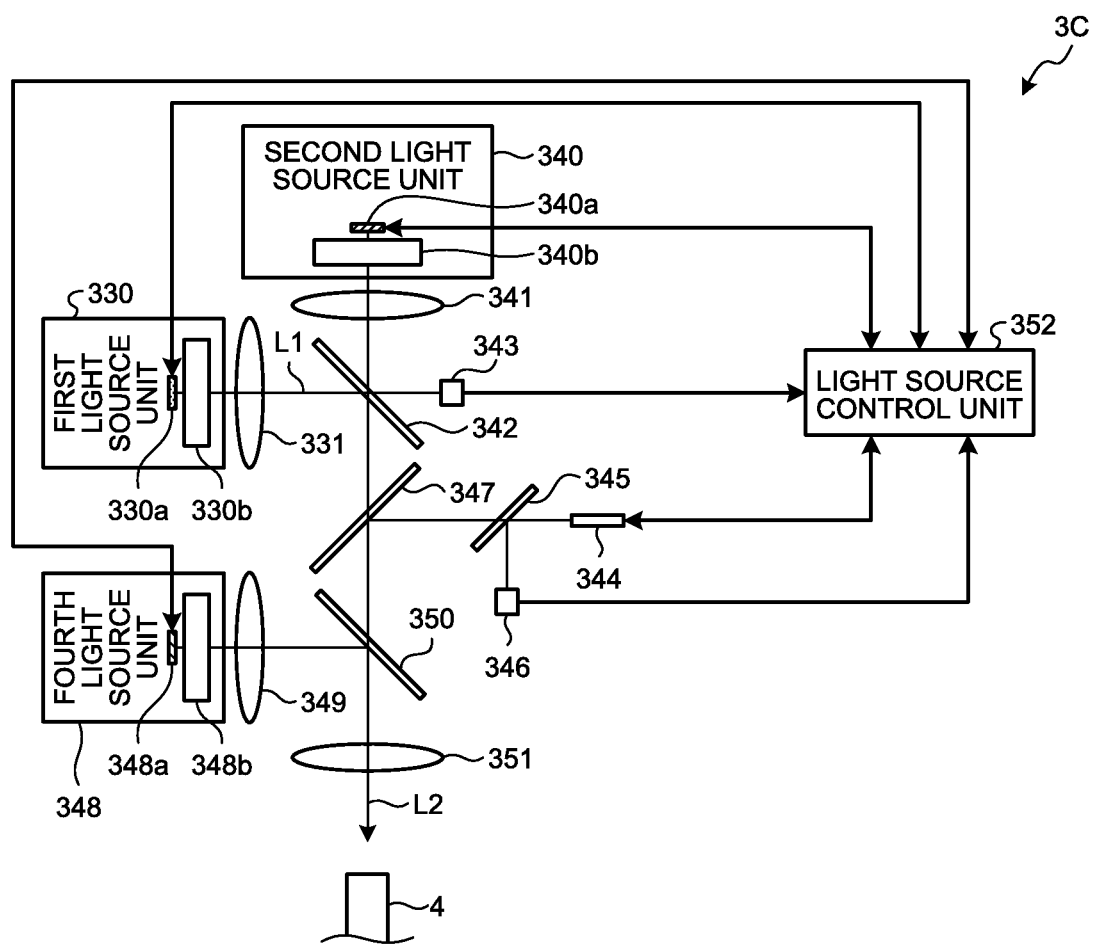
FIG. 6 is a schematic view illustrating a schematic configuration of a light source device according to a fourth embodiment.

FIG. 6 is a schematic view illustrating a schematic configuration of the light source device according to the fourth embodiment. A light source device 3C illustrated in FIG. 6, a first light source unit 330, a first condenser lens 331, a second light source unit 340, a second condenser lens 341, a first optical member 342, a first detecting unit 343, a third light source unit 344, a second optical member 345, a second detecting unit 346, a third optical member 347, a fourth light source unit 348, a third condenser lens 349, a fourth optical member 350, a fourth condenser lens 351, and a light source control unit 352.

The first light source unit 330 emits the first light including the light of the green wavelength band under the control of the light source control unit 352. The first light source unit 330 includes a green LED element 330a that emits the light of the green wavelength band, and a fluorescent body 330b that emits green light by receiving the green light that is emitted from the green LED element 330a.

The first condenser lens 331 condenses and emits the first light emitted from the first light source unit 330 towards the first optical member 342. The first condenser lens 331 is configured by using one or a plurality of lenses.

The second light source unit 340 emits the second light including the specific wavelength (the green wavelength band) included in the first light towards the first optical member 342 under the control of the light source control unit 352. Specifically, the second light source unit 340 emits the light of the white wavelength band as the second light. The second light source unit 340 includes a blue LED element 340a that emits the light of the blue wavelength band (a wavelength band of 435 nm to 480 nm), and a yellow fluorescent body 340b that emits white light by receiving the blue light that is emitted from the blue LED element 340a. Note that, it is sufficient that the second light source unit 340 may emit the white light as the second light, and the second light source unit 340, for example, may be a white light LED element, a light emitting element including a violet LED that emits light of a violet wavelength band and a fluorescent body that emits white light by receiving violet light, a xenon lamp, or the like.

The second condenser lens 341 condenses and emits the second light emitted from the second light source unit 340 towards the first optical member 342. The second condenser lens 341 is configured by using one or a plurality of lenses.

The first optical member 342 is configured by using a reflection filter such as dichroic mirror. The first optical member 342 transmits the light of the specific wavelength band in the first light emitted from the first light source unit 330 through the first condenser lens 331 towards the first detecting unit 343, and transmits the second light emitted from the second light source unit 340 through the second condenser lens 341 in a direction different from that of the light of the specific wavelength band (the direction of the light guide 4). Further, the first optical member 342 reflects the transmitted light of the wavelength band different from the specific wavelength band in a direction in which the second light is transmitted (the direction of the light guide 4). Specifically, the first optical member 342 transmits a part of the light of the green wavelength band that is the specific wavelength band included in the first light emitted from the first light source unit 330 to the first detecting unit 343, reflects the remaining light in the direction of the light guide 4, and transmits the second light emitted from the second light source unit 340 in the direction of the light guide 4.

The first detecting unit 343 is configured by using an optical sensor such as a photodiode. The first detecting unit 343 detects the amount of a part of the first light transmitted through the first optical member 342 that is the light of the specific wavelength band transmitted through the first optical member 342, and outputs the detection result to the light source control unit 352.

The third light source unit 344 emits the light for compensating a part of the light of the specific wavelength band transmitted through the first optical member 342 under the control of the light source control unit 352. Specifically, the third light source unit 344 emits the light of the green wavelength band. The third light source unit 344 is configured by using a green LD element or fiber.

The second optical member 345 is configured by using a reflection filter such as dichroic mirror. The second optical member 345 reflects a part of the light emitted from the third light source unit 344 to the second detecting unit 346, and transmits the remaining light to the third optical member 347.

The second detecting unit 346 is configured by using an optical sensor such as a photodiode. The second detecting unit 346 detects the amount of a part of the light reflected from the second optical member 345, and outputs the detection result to the light source control unit 352.

The third optical member 347 is configured by using a reflection filter such as dichroic mirror. The third optical member 347 multiplexes the light transmitted through the first optical member 342 and the light transmitted through the second optical member 345 to emit towards the fourth optical member 350.

The fourth light source unit 348 emits the light of the red wavelength band under the control of the light source control unit 352. The fourth light source unit 348 includes a red LED element 348a that emits the light of the red wavelength band, and a fluorescent body 348b that emits red light by receiving the red light that is emitted from the red LED element 348a.

The third condenser lens 349 condenses the light emitted from the fourth light source unit 348 to emit towards the fourth optical member 350. The third condenser lens 349 is configured by using one or a plurality of lenses.

The fourth optical member 350 multiplexes the light emitted from the third condenser lens 349 and the light transmitted through the third optical member 347 to emit towards the fourth condenser lens 351.

The fourth condenser lens 351 condenses the light emitted from the fourth optical member 350 on the light path L2 to emit into the light guide 4. The fourth condenser lens 351 is configured by using one or a plurality of lenses.

The light source control unit 352 is configured by using a processor including a memory, and hardware such as a CPU, an FPGA, and an ASIC. The light source control unit 352 controls the amount of emitted light from each of the first light source unit 330, the second light source unit 340, the third light source unit 344, and the fourth light source unit 348, based on the detection result of each of the first detecting unit 343 and the second detecting unit 346. Specifically, the light source control unit 352 performs control such that the amount of emitted light from each of the first light source unit 330, the second light source unit 340, the third light source unit 344, and the fourth light source unit 348 is at a constant ratio, based on the detection result each of the first detecting unit 343 and the second detecting unit 346. Note that, the light source control unit 352 performs the same processing as that of the light source control unit 309 according to the first embodiment described above.

According to the fourth embodiment described above, the light source control unit 352 controls the first light source unit 330, the second light source unit 340, the third light source unit 344, and the fourth light source unit 348, based on the detection result of the first detecting unit 343 and the detection result of the second detecting unit 346, and thus, as with the first embodiment described above, it is possible to maintain the color balance, the brightness, and the color taste of the white light.

Note that, in the third embodiment, the first optical member 342 transmits a part of the light of the green wavelength band that is the first light towards the first detecting unit 343, but the present disclosure is not limited thereto, and for example, the optical properties of the first optical member 342 may be changed to optical properties in which a part of the light of the red wavelength band or the light of the blue wavelength band is transmitted. That is, in the third embodiment, the optical properties of the first optical member 342 and the light emitted from the first light source unit 330 and the third light source unit 344 may be suitably changed in accordance with the wavelength band of the light detected by the first detecting unit 343.

Fifth Embodiment

Next, a fifth embodiment will be described. In the first embodiment to the fourth embodiment described above, the case of being applied to the rigid endoscope system using the rigid endoscope has been described, but in the fifth embodiment, the case of being applied to a flexible endoscope system using a flexible endoscope will be described. Note that, the same reference numerals will be applied to the same configurations as those of the endoscope system 1 according to the first embodiment described above, and the detailed description thereof will be omitted.

Schematic Configuration of Endoscope System

Figure 7:
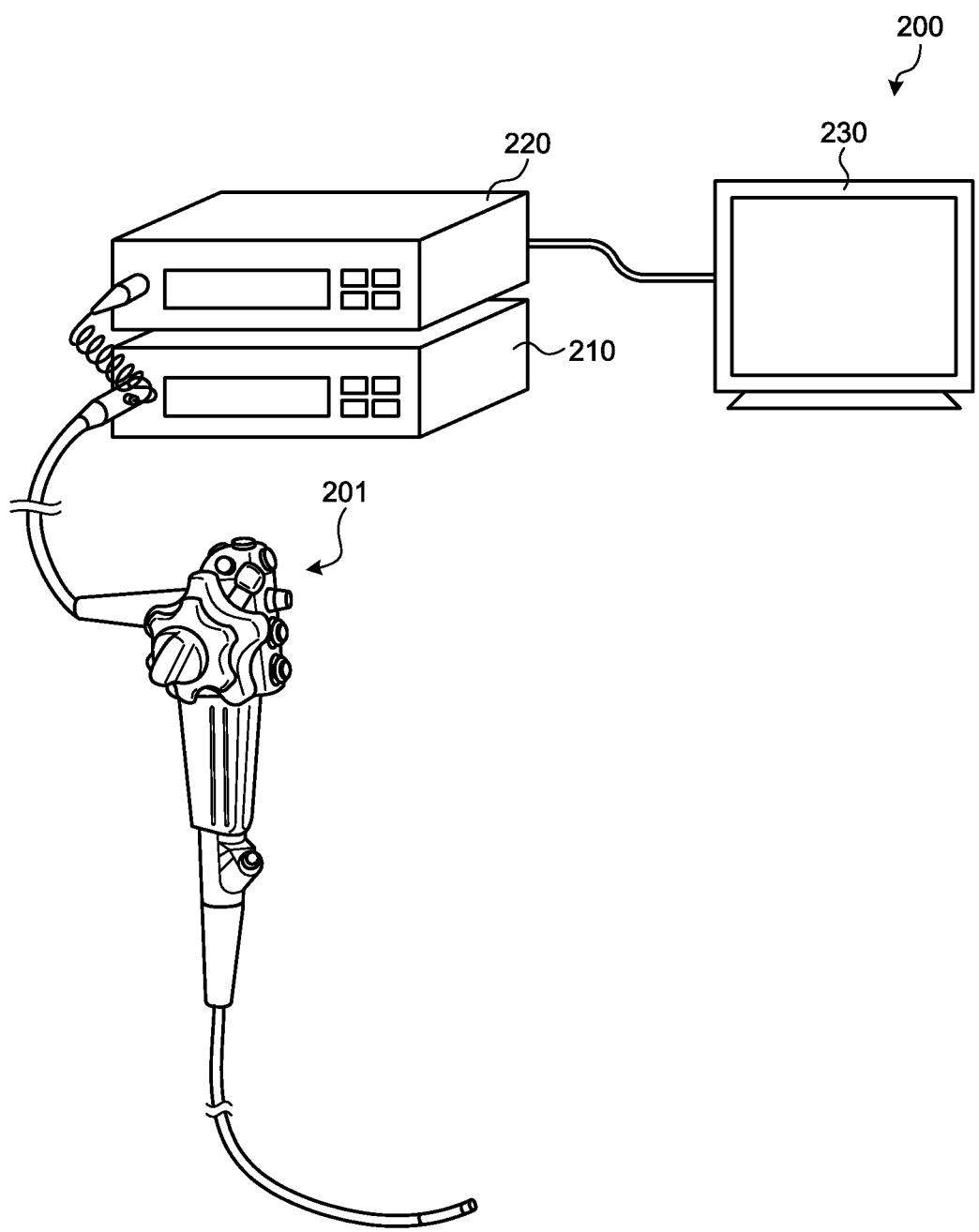
FIG. 7 is a diagram illustrating a schematic configuration of an endoscope system according to a fifth embodiment.

FIG. 7 is a diagram illustrating a schematic configuration of the endoscope system according to the fifth embodiment. An endoscope system 200 illustrated in FIG. 7, an endoscope 201 that captures an in-vivo image of an observed region by inserting an insertion portion into the subject, and generates an imaging signal, a light source device 210 that supplies white light or infrared light to the endoscope 201, a control device 220 that performs predetermined image processing with respect to the imaging signal acquired by the endoscope 201, and comprehensively controls the entire operation of the endoscope system 200, and a display device 230 that displays the in-vivo image subjected to the image processing by the control device 220.

The light source device 210 has at least the same configuration as that of any one of the light source devices 3 to 3C of the first embodiment to the fourth embodiment described above.

According to the fifth embodiment described above, even in the flexible endoscope system 200, it is possible to obtain the same effect as that of the first embodiment described above.

Sixth Embodiment

Next, a sixth embodiment will be described. In the first embodiment to the fourth embodiment described above, the case of being applied to the endoscope system has been described, but in the sixth embodiment, the case of being applied to a surgical microscope system will be described. Note that, the same reference numerals will be applied to the same configurations as those of the endoscope system 1 according to the first embodiment described above, and the detailed description thereof will be omitted.

Configuration of Surgical Microscope System

Figure 8:
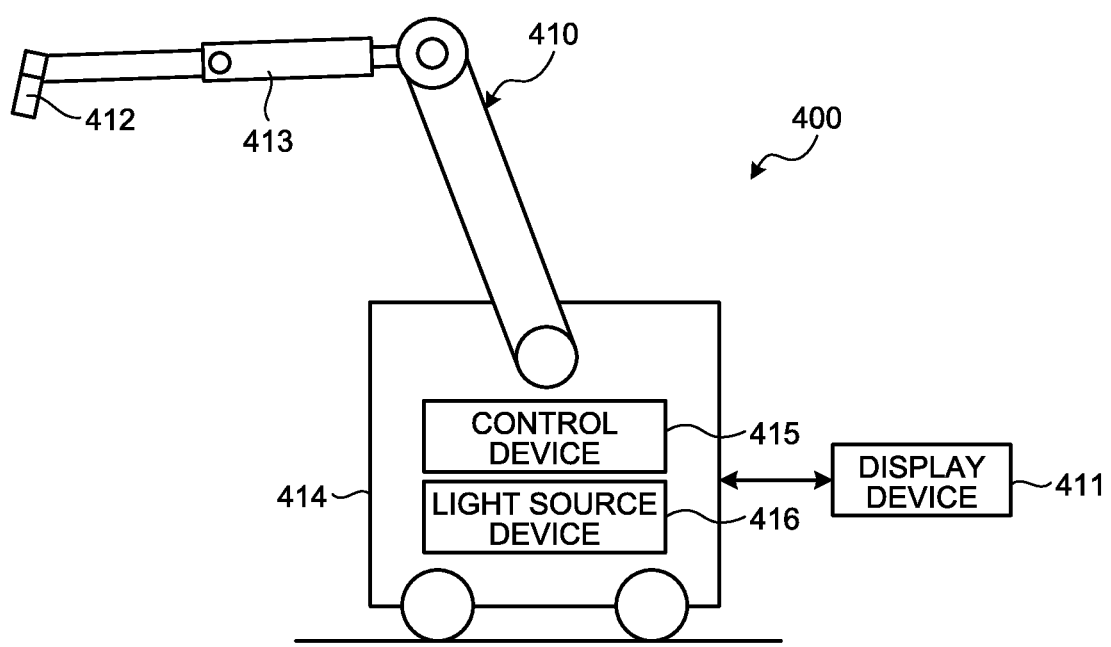
FIG. 8 is a diagram illustrating a schematic configuration of a surgical microscope system according to a sixth embodiment.

FIG. 8 is a diagram illustrating a schematic configuration of the surgical microscope system according to the sixth embodiment. A surgical microscope system 400 illustrated in FIG. 8 includes a microscope device 410 that is a medical imaging device acquiring an image for observing an object by image capturing, and a microscope device 410 that displays the image captured by a display device 411. Note that, the display device 411 and the microscope device 410 may also be integrally configured.

The microscope device 410 includes a microscope unit 412 that performs imaging by enlarging a minute site of the object, a support portion 413 that is connected to a proximal end portion of the microscope unit 412, and includes an arm rotatably supporting the microscope unit 412, and a base portion 414 that rotatably retains a proximal end portion of the support portion 413, and is movable on a floor surface. The base portion 414 includes a control device 415 that controls the operation of the surgical microscope system 400, and a light source device 416 that generates white light or the like to be emitted to the object from the microscope device 410. Note that, the light source device 416 has at least the same configuration as that of any one of the first embodiment to the fourth embodiment described above. In addition, the base portion 414 may be configured to support the support portion 413 by being fixed to a ceiling, a wall surface, or the like, instead of being provided to be movable on the floor surface.

The microscope unit 412, for example, is in the shape of a cylinder, and includes a lens unit and an imaging unit therein. A switch that receives the input of an operation instruction of the microscope device 410 is provided on a lateral surface of the microscope unit 412. Cover glass for protecting the inside is provided an aperture surface of a lower end portion of the microscope unit 412 (not illustrated).

The surgical microscope system 400 configured as described above moves the microscope unit 412, performs a zoom manipulation, or switches the illumination light while manipulating various switches in a state where a user such as an operator holds the microscope unit 412. Note that, it is preferable that the shape of the microscope unit 412 is a shape that is elongated in an observation direction such that a visual field direction is easily changed by being held by the user. For this reason, the shape of the microscope unit 412 may be a shape other than a cylindrical shape, and for example, may be a polygonal columnar shape.

According to the sixth embodiment described above, in the surgical microscope system 400, it is possible to obtain the same effect as that of the first embodiment described above.

Other Embodiments

It is possible to form variations by suitably combining a plurality of constituents disclosed in the medical observation system according to the first embodiment to the sixth embodiment of the present disclosure described above. For example, some constituents may be deleted from all of the constituents described in the medical observation system according to the first embodiment to the sixth embodiment of the present disclosure described above. Further, the constituents described in the medical observation system according to the first embodiment to the sixth embodiment of the present disclosure described above may be suitably combined.

In addition, in the medical observation system according to the first embodiment to the sixth embodiment of the present disclosure, the "unit" that has been described above may be replaced with "means", a "circuit", or the like. For example, the control unit may be replaced with control means or a control circuit.

In addition, a program that is executed by the medical observation system according to the first embodiment to the sixth embodiment of the present disclosure is provided by being recorded in a computer readable recording medium such as a CD-ROM, a flexible disk (FD), a CD-R, a digital versatile disk (DVD), a USB medium, and a flash memory, in file data in an installable format or an executable format.

In addition, the program that is executed by the medical observation system according to the first embodiment to the sixth embodiment of the present disclosure may be stored on a computer that is connected to a network such as the internet, and may be provided by being downloaded through the network.

Note that, herein, in the description of a timing chart, an anteroposterior relationship of the processings between timings is specified by using the expression of "first", "after that", "subsequently", and the like, but the order of the processing for implementing the present disclosure is not uniquely set by the expression. That is, here, the order of the processings in the timing chart may be changed within a consistent range.

According to the present disclosure, an effect is obtained in which even when light rays from each light emitting element are multiplexed on a light path, a color balance may be maintained.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A light source device comprising:
    a first light source configured to emit first light including a white wavelength band or two or more wavelength bands of at least red, green, and blue;
    a second light source configured to emit second light including a specific wavelength band included in the first light;
    a first detector configured to detect an amount of the light of the specific wavelength band in the first light;
    a first optical member configured to multiplex light of a wavelength band different from the specific wavelength band in the first light, and the second light;
    a second optical member disposed between the first optical member and the second light source, and configured to reflect or transmit a part of the second light;
    a second detector configured to detect an amount of a part of the second light reflected or transmitted by the second optical member;
    and
    a processor configured to:
    control a brightness of the first light source based on a detection result of the first detector and a detection result of the second detector, and
    control a brightness of the second light source based on the detection result of the first detector and the detection result of the second detector, to control a color balance of a light multiplexed by the first light emitted from the first light source and the second light emitted from the second light source such that a constant ratio between an amount of light output from the first light source and an amount of light output from the second light source is maintained.

2. The light source device according to claim 1, wherein the second light source is configured to emit the second light towards the first optical member, and
    the first optical member is configured to emit the light of the specific wavelength band in the first light towards the first detector, and multiplex the light of the wavelength band different from the specific wavelength band in the first light, and the second light.

3. The light source device according to claim 1, wherein the first optical member is configured to
    reflect the light of the specific wavelength band towards the first detector,
    transmit the light of the wavelength band different from the specific wavelength band, and
    reflect the second light in a direction in which the light of the wavelength band different from the specific wavelength band is transmitted.

4. The light source device according to claim 1, wherein the first optical member is configured to
    transmit the light of the specific wavelength band towards the first detector,
    transmit the second light in a direction different from a direction of the light of the specific wavelength band, and reflect the light of the wavelength band different from the specific wavelength band in the direction in which the second light is transmitted.

5. The light source device according to claim 1, further comprising a third optical member disposed on a light path of the first light between the first light source and the first optical member, and configured to emit the light of the specific wavelength band in the first light into the first detector and emit the light of the wavelength band different from the specific wavelength band in the first light into the first optical member.

6. The light source device according to claim 1, wherein the light of the specific wavelength band is light of a wavelength band of any one of red, green, and blue.

7. A medical observation system comprising:
the light source device according to claim 1; and
an endoscope including an imaging device configured to generate an imaging signal and disposed in a distal end portion of an insertion portion of the endoscope for being inserted into a subject,
wherein the light source device is configured to supply, to the endoscope, light in which the light of the wavelength band different from the specific wavelength band, and the second light are multiplexed.

8. An illumination method comprising:
emitting first light including a white wavelength band or two or more wavelength bands of at least red, green, and blue;
emitting second light including a specific wavelength band included in the first light;
detecting an amount of the light of the specific wavelength band in the first light;
reflecting or transmitting a part of the second light;
detecting the part of the second light;
multiplexing light of a wavelength band different from the specific wavelength band in the first light, and a remaining part of the second light;
controlling a brightness of the first light based on detection results of detecting the amount of the light of the specific wavelength band in the first light and detecting the part of the second light; and
controlling a brightness of the second light based on the detection results of detecting the amount of the light of the specific wavelength band in the first light and detecting the part of the second light, including controlling a color balance of a light multiplexed by the first light emitted and the second light emitted such that a constant ratio between an amount of the first light and an amount of the second light is maintained.

9. A non-transitory computer readable recording medium on which an executable program for controlling a light source device, the light source device including: a processor; a first light source configured to emit first light including a white wavelength band or one or more wavelength bands of at least red, green, and blue; a second light source configured to emit second light including a specific wavelength band included in the first light; a first detector configured to detect an amount of the light of the specific wavelength band in the first light; a first optical member configured to multiplex light of a wavelength band different from the specific wavelength band in the first light, and the second light source, a second optical member disposed between the first optical member and the second light source, and configured to reflect or transmit a part of the second light; and a second detector configured to detect an amount of a part of the second light reflected or transmitted by the second optical member, the program instructing the processor to execute:
controlling a brightness of the first light source based on a detection result of the first detector and a detection result of the second detector, and
controlling a brightness of the second light source based on the detection result of the first detector and the detection result of the second detector, including controlling a color balance of a light multiplexed by the first light emitted and the second light emitted such that a constant ratio between an amount of light output from the first light source and an amount of light output from the second light source is maintained.

* * * * *